United States Patent
Abadi

[19]

[11] Patent Number: 5,596,997
[45] Date of Patent: Jan. 28, 1997

[54] PANTY CONDOM

[76] Inventor: Max M. Abadi, Carrera 68 No. 21-85, Santafé de Bogotá, Colombia

[21] Appl. No.: 491,741

[22] Filed: Jun. 19, 1995

[51] Int. Cl.$^6$ .......................................... A61F 6/04
[52] U.S. Cl. .......................................... 128/844; 128/918
[58] Field of Search .................... 128/842, 844, 128/918; 604/347–353

[56] References Cited

U.S. PATENT DOCUMENTS

| | | |
|---|---|---|
| 899,251 | 9/1908 | Graham . |
| 1,986,504 | 1/1935 | Cubbon . |
| 2,309,868 | 2/1943 | Robertson . |
| 3,102,541 | 9/1963 | Adams . |
| 3,536,066 | 10/1970 | Ludwig . |
| 4,004,591 | 1/1977 | Freimark . |
| 4,167,183 | 9/1979 | Barlow . |
| 4,508,114 | 4/1985 | Pennystone . |
| 4,576,156 | 3/1986 | Dyck et al. . |
| 4,630,602 | 12/1986 | Strickman et al. . |
| 4,664,104 | 5/1987 | Jaicks . |
| 4,735,621 | 4/1988 | Hessel . |
| 4,808,174 | 2/1989 | Sorkin . |
| 4,817,593 | 4/1989 | Taller et al. . |
| 4,834,114 | 5/1989 | Boarman ................... 128/844 |
| 4,840,624 | 6/1989 | Lee . |
| 4,855,169 | 8/1989 | McGlothlin . |
| 4,867,176 | 9/1989 | Lash . |
| 4,898,184 | 2/1990 | Skurkovich et al. . |
| 4,942,885 | 7/1990 | Davis ................... 128/844 |
| 4,955,392 | 9/1990 | Sorkin . |
| 4,981,147 | 1/1991 | Barnett ................... 128/844 |
| 5,193,555 | 3/1993 | Richardson et al. . |
| 5,325,871 | 7/1994 | Reddy . |
| 5,413,117 | 5/1995 | Wills ................... 128/842 |

*Primary Examiner*—Michael A. Brown
*Attorney, Agent, or Firm*—Vaden, Eickenroht & Thompson

[57] ABSTRACT

A female panty condom having a panty having an opening generally at the genital area of the wearer and located approximately over the vagina of the wearer. A pouch including a front side having a slit and a back side having a slit is affixed to the panty such that the opening in the panty, the slit in the front side of the pouch and the slit in the back side of the pouch are aligned. A sheath is positioned within the pouch behind the slit in the front side of the pouch such that the penis of a male partner may enter the opening of the sheath through the opening in the panty. The sheath will extend to cover the penis as it moves through the slit in the back side of the pouch and into the vagina of the wearer.

13 Claims, 2 Drawing Sheets

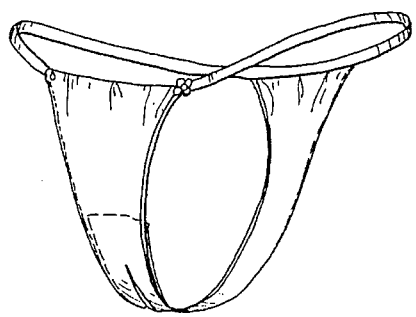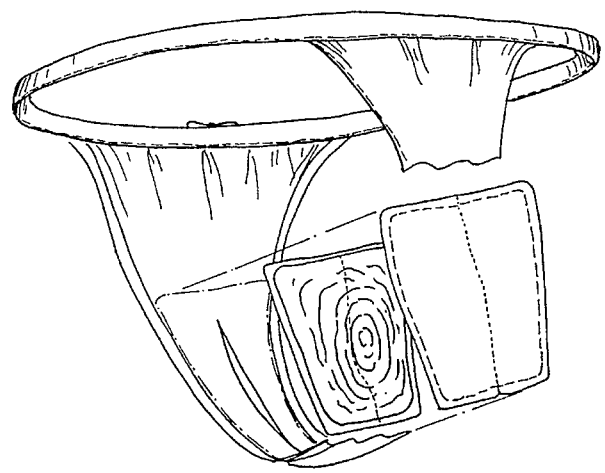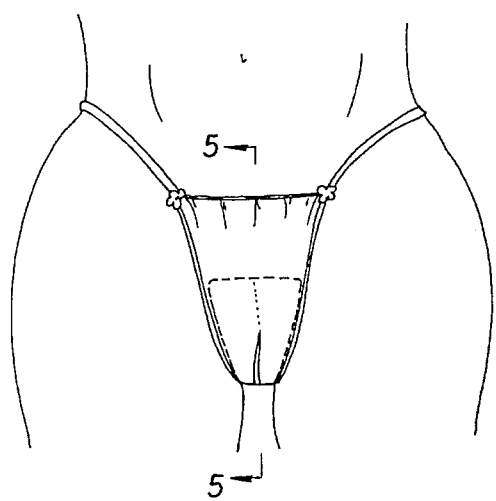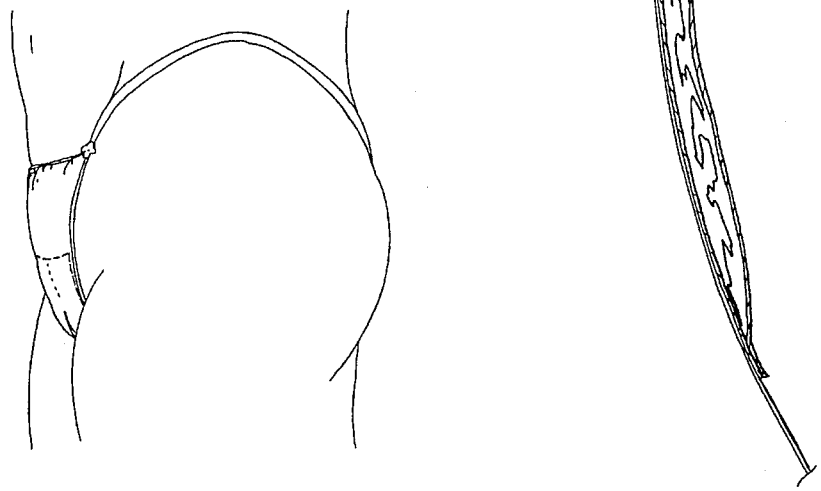

FIG. 6
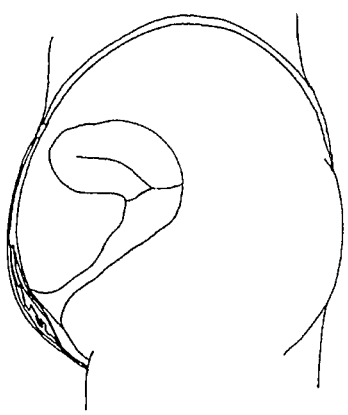
FIG. 7
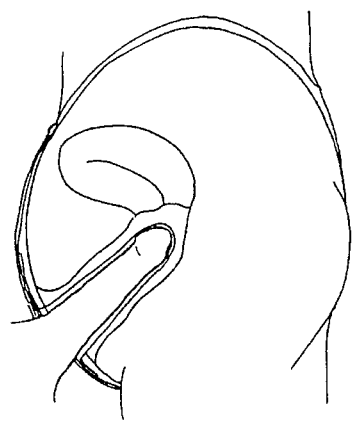
FIG. 8
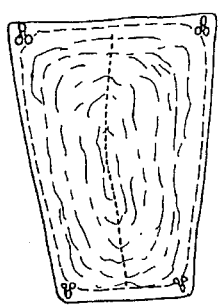
FIG. 9
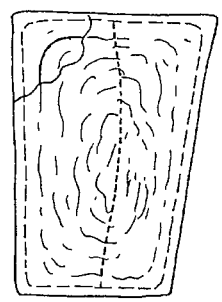
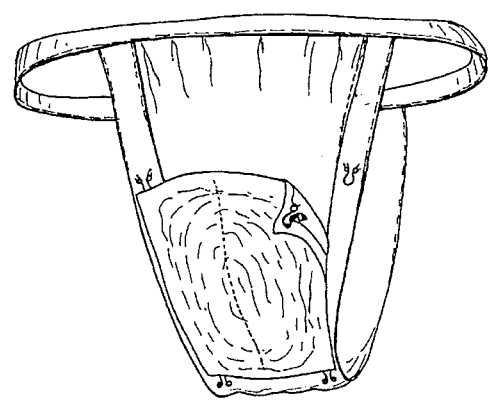
FIG. 10

PANTY CONDOM

FIELD OF THE INVENTION

The following invention relates generally to a female barrier contraceptive. Particularly, the invention relates to a female panty condom not requiring an insertion applicator and is suitable for being worn for extended lengths of time, such as throughout the day.

DESCRIPTION OF THE PRIOR ART

Since medieval times, the concept of the condom as a means to prevent the man's semen from being deposited in the woman's cervix, and hence preventing insemination, is known. Aside from being a birth control method, another main purpose of the condom is to prevent sexually transmitted diseases, such as syphilis, gonorrhea, chlamydia, herpes, and of great interest currently, the acquired immune deficiency syndrome (AIDS). Given its public health importance, the condom has had to evolve in different ways and according to the user's necessities.

Currently, the most known condom is certainly the male version manufactured out of latex which the user unrolls to cover the penis from its head to the pubic base. Other materials have also been used, like polyurethane, which is stronger than latex and does not degrade as easily; however, one encounters heat transfer and sensitivity problems with the use of polyurethane. Likewise, condoms made of other elastomers, polyolefins or combinations of these have been proposed. For example, see U.S. Pat. Nos. 4,855,169 (McGlthlin, et al.), 4,808,174 (Sorkin), 4,817,593 (Taller, et al.) and 4,576,156 (Dyck, et al.).

Female versions of the male counterpart have also entered the market as an alternative for female users who want to be able to use some sort of barrier birth control method, and where classical female barrier methods are not sufficiently effective (e.g. the diaphragm). One female condom already in the market is known as Reality® and is manufactured by Chartex International PLC. This female condom is described in U.S. Pat. No. 4,735,621 and is manufactured from polyurethane. Shortcomings of this condom include problems with placement (the condom must be inserted before coitus) and subsequent shifting, lack of sensation and heat transfer for both the male and female user given the characteristics and thickness of the polyurethane, emission of awkward sounds during coitus and the relatively high price of each individual condom. Additionally, given this female condom includes two rings, an outer one to keep the condom in place over the vaginal entrance, and an inner one to keep the condom from slipping out of the vagina, problems such as: 1) the outer ring being pushed into the vagina, 2) the inner ring causing discomfort for both the female and male user, and 3) the penis slipping around the edge of the outer ring and thus penetrating the vagina unprotected, may occur.

Male and female condoms for the prevention of the transmission of AIDS and venereal diseases are disclosed in U.S. Pat. No. 4,898,184 (Skukovich et al.). The female condom comprises an elongated part which is inserted into the vagina and external apron-like parts for covering the external genitalia, pubic, lower abdomen, inner thighs, and perineum. The elongated part is inserted into the vagina using an insertion device. The female condom is not conveniently used, and unless the apron-like parts are attached to the skin using a weak adhesive, the apron-like parts move freely and not provide the desired protection against the transmission of disease.

U.S. Pat. No. 4,664,104 (Jaicks) discloses an anti-herpes modality system for protecting both male and female partners against the passage of the herpes virus. The system may include a female garment having a circular hole with a rim portion at the genital area. A male sheath member may be connected to the rim portion of the circular hole of the garment. The rim is secured to a biasable toroidal lock member, and the edge of the sheath is secured to a toroidal gripper member held by the toroidal lock member. The lock member is made of plastic, rubber, or a coiled spring capable of radially biasing against the penis of the male partner. The lock member must be relatively rigid, and when the sheath is connected to the gripper member, a ridge is formed by the rigid rim, lock and gripper members. The rigid rim makes the garment uncomfortable to the wearer, thus making the garment unsuitable for wear during extended periods of time. Moreover, the sheath is not easily and conveniently positioned, and a lubricant cannot be maintained in association with the device.

U.S. Pat. No. 4,840,624 (Lee) discloses a female condom device having a pubic area cover pad with a condom attached perpendicularly to the cover pad. Leg encircling tapes attached to the pad and held by a waist belt position the device. An insertion device is provided for assistance in positioning the condom portion inside the vagina. Other female condoms in the prior art have similar shortcomings such as requiring placement systems or insertion devices in order to insert the condom inside the vagina (see e.g. U.S. Pat. Nos. 5,325,871 (Reddy), 5,193,555 (Richardson, et al.) and 4,867,176 (Lash).

Thus, there remains a need for a female contraceptive device that provides protection against the transfer of body fluids between partners during sexual intercourse, which can be comfortably worn by the female partner for extended lengths of time, and is readily available for use without having to use applicators, insertion devices, or apply lubricants.

BRIEF DESCRIPTION OF THE INVENTION

An object of the present invention is to solve the problems of the prior art by presenting a female panty condom having a sheath made of a secure material, but at the same time being thin, sensitive and with good heat transfer.

Another object of the present invention is to present a panty condom which incorporates a system that permits the sheath to be fitted comfortably, easily and minimizing any subsequent shifting.

Yet another object of the present invention is to present a panty condom which can be worn throughout the day and which does not require a separate applicator device to insert.

Other objects, and the advantages, of the present invention will be made clear to those skilled in the art from a review of the following detailed description of the preferred embodiments thereof.

The following invention is a female barrier contraceptive chiefly characterized by the union of a sheath, manufactured out of a polyolefinic material, preferably a low density polyethylene, with a pair of female underwear, commonly known as a panty. The opening of the sheath is attached to the crotch area of the panty, where an opening or slit in the panty fabric allows the penis to penetrate and be inserted into the sheath and eventually into the vagina.

In a preferred embodiment, the sheath is covered with a lubricant to increase lubrication inside and outside the sheath. In this embodiment, in order to prevent the lubricant from spreading onto the rest of the panty and the genital area of the woman, a protective pouch (preferably with a cotton backing to prevent skin-plastic contact) located in the crotch area is used to cover the sheath coated with the lubricant. In the preferred embodiment, the pouch has a pre-perforated slit down the middle of each side which is easily torn open when the penis penetrates the panty slit and the sheath. Following use, the panty with the attached sheath are thrown away.

In another embodiment, the panty may be reusable. In this embodiment, the sheath, enclosed in its protective pouch, contains a means to attach itself to the crotch area of the panty. In this manner, after intercourse, the sheath and protective pouch can be discarded and the panty section washed and used again.

Use of the panty condom disclosed herein is very easy as it only requires donning the pair of panties, and does not involve any prior preparation during foreplay. When the penis pushes against the crotch area of the panty, the penis slides through the opening in the panty and the slit opening in the pouch and the sheath is extended into the vagina along with the penis. There is no need for an external and separate applicator device. Because of the nature of the polyethylene (or other polyolefin) in combination with the internal lubrication of the condom, the condom tends to stay inside the vagina even as the penis slips out, thus obviating any need for any internal fixation of the sheath to the vagina, or of the sheath to the penis.

The expression "panty condom" as used herein, refers to the complete barrier contraceptive described in the specification and claims, including the panty and sheath. The word "sheath" as used herein, refers to the section of the panty condom which actually surrounds the penis when the same penetrates the vagina.

DESCRIPTION OF THE DRAWINGS

FIG. 1 is a perspective view of a panty condom in accordance with a first embodiment of the present invention.

FIG. 1a is a perspective view of a panty condom in accordance with another embodiment of the present invention.

FIG. 2 is an exploded perspective view of the embodiment of the present invention shown in FIG. 1.

FIG. 3 is a front view of the panty condom of FIG. 1 being worn by a user.

FIG. 4 is a side view of the panty condom being worn by a user of the invention.

FIG. 5 is a cross-sectional view of the panty condom of FIG. 3 taken along lines 5—5.

FIG. 6 is a sagittal view of the wearer's pelvic region illustrating the position of the panty condom when worn.

FIG. 7 is a sagittal view of the wearer's pelvic region illustrating the panty condom during use.

FIG. 8 is a front view of the protective pouch of the panty condom shown in FIG. 2.

FIG. 9 is a rear view of the protective pouch.

FIG. 10 is a perspective view of a panty condom in accordance with an alternate embodiment of the invention.

DETAILED DESCRIPTION OF THE INVENTION

The female panty condom described herein provides an improved method of female barrier birth control. As seen in FIG. 1 and FIG. 1a, the female panty condom shown generally as 10 includes a female panty 12. Panty 12 is preferably made of natural fabrics. However, nylon and other fabrics known for use in making female panties may be used. A sheath 14 is secured to the panty such that during coitus the sheath extends to cover the body of the penis of the male partner, as can be seen in FIG. 7.

Referring to FIG. 1a, sheath 14 may be sewn directly to the panty at sew lines 44, or contained within a protective pouch 16, shown, for example, in FIG. 1. Sheath 14 may also be affixed directly to the panty using other means known to those in the art. Sheath 14 is folded in an accordion-like manner behind lip 40 so that it readily unfolds to cover the penis of the male partner. When attaching the sheath directly to the panty, it was found that folding the lip of the sheath's opening over itself various times, and then forming the thickened lip into the form of a square or rectangle, worked best when attaching the sheath onto the crotch area of the panties.

In the preferred embodiment of FIG. 1, sheath 14 is folded up and positioned inside protective pouch 16 as shown in FIGS. 2, 5 and 9. Protective pouch 16 is then affixed to panty 10, as will be discussed below. Sheath 14 is preferably manufactured from a polyolefin, preferably a low density polyethylene, which principally permits a marked increasing in sensitivity and heat transfer for the users. Moreover, the use of a polyolefin: (a) permits sheath 14 to be used without any sort of internal retention means (for example, without need for a ring inside the vagina); (b) permits the penis to enter sheath 14 when it is folded so that it extends over the penis as it penetrates the vagina (i.e. no pre-insertion by the woman or applicator device is required and thus there is no interruption of foreplay); and (c) greatly reduces the noise generally created by other female condoms which are made from a material such as polyurethane. The use of a polyolefin, such as low density polyethylene, also demonstrates excellent adhesion which permits the walls of the sheath to be in contact with the penis and the walls of the vagina (when the penis lies inside the vagina), thereby significantly increasing the sensitivity for the users.

Additionally, the cost of the panty condom described herein is reduced significantly over the female condoms in the prior art, as the cost of polyethylene is markedly less than for polyurethane. After experimenting, the preferable wall thickness for the sheath was of 0.0003 inches, which in turn is an order of magnitude ten times thinner than latex condoms which have thicknesses of approximately 0.0040 inches. At these dimensions, the tensile strength of polyethylene is substantially greater than latex.

The sheath 14 can be produced by using a high quality polyethylene film (Mobilwrap MAX and F made by Mobil Oil Corporation have worked satisfactorily) and stretching it over a mold until the desired shape and wall thickness are reached, applying concepts well known by those versed in the prior art.

Referring to FIG. 1, panty 10 has a slit-shaped opening 18 in the crotch area located approximately over the entrance to the vagina. Slit 18 should be long enough and cut appropriately so that when stretched, it will not cause any discomfort to the male partner. In cases where a lubricant is to be used with sheath 14, it is desirable to use protective pouch 16 to hold the sheath in the panty's crotch area when not in use. Protective pouch 16 also prevents lubricant from seeping out of the pouch and accessing the woman's genital area or the rest of the panties. In this preferred embodiment, protective pouch 16 is formed by attaching a first plastic sheet or front side of the pouch 16a to a second plastic sheet or back side of the pouch 16b, shown in FIGS. 8 and 9, respectively. Sides 16a and 16b are attached to each other along their edges and over the thickened lip 40 of folded up sheath 14, thereby enclosing sheath 14 and the lubricant within pouch 16. Front side 16a and back side 16b may be sewn together. Alternatively the sides may be heated at their edges to melt seal the sides together. Once the sides are sealed, heat may be applied to front side 16a over lip 40 to seal the lip to front side 16a and thus hold sheath 14 in place within pouch 16.

As seen in FIGS. 8 and 9, sides 16a and 16b each have a longitudinal slit opening 20 and 22, respectively, down the middle. Slits 20 and 22 are positioned parallel to and directly over the panty opening 18. Longitudinal slits 20 and 22 can be kept shut using any conventional method known in the art, but it is desirable to use pre-perforated slits, thereby allowing the penis to pierce slit 20 then slit 22 with slight pressure, while maintaining the lubricant within protective pouch 16 under reasonable forces generated in the crotch area.

Additionally, and making reference to FIG. 2, it is preferred to affix a cloth backing 24 with a slit opening 26 over the protective pouch. Cloth backing 24 will eliminate discomfort to the user caused by skin-plastic contact during prolonged wear. It is recommended that cloth backing 24 also be placed over sheath 14 when it is not held in a protective pouch containing lubricant, for the same reasons already expressed. Cloth backing 24 is preferably made from a natural fabric to provide maximum comfort to the wearer. Synthetic fabrics, however, may be used to make cloth backing 24. Cloth backing 24 are preferably sewn to panty 12 at sew lines 38 shown in FIG. 2. Alternatively, cloth backing 24 may be glued to panty 12 or the back of pouch 16.

The preferred embodiment of the female panty condom as worn by the female user is shown in FIGS. 3 and 4. Panty 12 is worn as any panty would be worn. Opening 18 is located over the vaginal opening of the wearer. Protective pouch 16 is preferably sewn to the inside of the crotch area of the panty at stitch lines 28. Alternatively, pouch 16 may be glued or affixed to the panty using means known to those skilled in the art. In the alternate embodiment shown in FIG. 10, pouch 16 is removably affixed to the outside of the crotch area of panty 12 by clips 30, 32, 34, and 36.

FIG. 5 shows an enlarged cross section of the preferred panty 12, protective pouch 16 with front side 16a and back side 16b, sheath 14, and cloth backing 24, taken along lines 5—5 of FIG. 3. When panty 12 is worn, slit 18 will be positioned over the vagina of the wearer. Protective pouch 16 is affixed to panty 12 such that slit 20 in front side 16a is aligned with slit 18. Sheath 14 is positioned within protective pouch 16. The open end of sheath 14, with rim or lip 40, seen in FIG. 9, is positioned against front side 16a of pouch 16 such that the penis of the male partner can enter opening 18, pass through slit 20 in front side 16a of the pouch and into the open end of sheath 14. Sheath 14 will extend to cover the penis as the penis moves through back side 16b of the pouch, then through slit 26 of cloth backing 24, and finally, into the vagina of the wearer of the panty condom.

FIG. 6 shows a cross section of the panty condom as worn and a sagittal view of the pelvic region of the wearer. Sheath 14 is positioned over the opening to the vagina. The panty condom is shown in place with sheath 14 still folded and tucked in its unused mode (in protective pouch 16) up against the entrance to the vagina.

Referring to FIG. 7, sheath 14 remains in position inside and outside the vagina during intercourse, thereby eliminating any external positional system such as an outer ring. Penis 42 is shown having penetrated panty opening 18, and passing through slit 20, into the open end of sheath 14, then through slit 22 and opening 26, (not labeled) and into the vagina covered by sheath 14.

For obvious sanitary reasons, the embodiments already described above are necessarily disposable, including the panty. Thus, in cases where the user wishes to recycle a panty, another embodiment of the invention permits the user to reuse a panty by employing a separate but attachable protective pouch and sheath. Making reference to FIG. 10, one can see how the protective pouch 16, enclosing sheath 14, forms a separate element, and having a means to attach itself to the panty 12, in this case four clips 30, 32, 34 and 36 located on each corner of protective pouch 16. One can also appreciate the perforated slit 20 which appears down the middle of the front side and slit 22 (not seen) which is down the back side of protective pouch 16. Thus, when the user wishes to employ the panty condom, she simply clips on protective pouch 16 to the appropriate panty. Thus, during sexual intercourse, the penis will pass through slit 20, enter the open end of sheath 14 which will extend to cover the penis, as it passes through slit 22, and opening 18, and enters the vagina. After use, the pouch 16 and extended sheath 14 are removed and disposed, leaving panty 12 available for future use.

By using the panty, one virtually eliminates the possibility that the sheath can be shoved into the vagina and stay inside, as is the case for other female and male condoms known in the art. Additionally, the combination essentially precludes any possibility of the penis slipping around sheath 14, which can occur in female condoms contained in the prior art. Moreover, the use of a panty significantly reduces pubic contact, and thus markedly minimizes sexually transmitted diseases having a known pubic transmission vector. Furthermore, the presence of the panty also minimizes the possibility that semen will be left in or around the vagina if the penis becomes flaccid and is pulled out, which can occur with other female and male condoms. Finally, the use of a panty allows the wearer to wear the contraceptive device all day if she wishes, thus eliminating both: (a) the need to carry around a separate device in a purse or the like, and (b) the need to don the contraceptive right before intercourse or during the middle of foreplay. Incidentally, this brings us back to another advantage of the panty condom, which is that it can be used for an extended period prior to intercourse (essentially, for as long a regular panty could be worn).

The foregoing description and drawings are only meant to better illustrate the invention, and should not be construed to restrict the scope of the invention in any way, as the true breadth of the invention shall be interpreted from the following claims.

I claim:

1. A female panty condom, comprising:

a panty having an opening generally at the genital area and located approximately over the vagina of a wearer; and a sheath having an open end, and a pouch connected to the panty for affixing the open end of the sheath over the opening in the panty, said pouch including a front side having a slit and a back side having a slit such that the opening, the slit in the front side of the pouch and the slit in the back side of the pouch are aligned such that a penis of a male partner can enter the open end through the opening in the panty, the sheath extending over the penis as it enters the vagina.

2. The female panty condom of claim 1, wherein the slit in the front side of the pouch and the slit in the back side of the pouch are perforated.

3. The female panty condom of claim 1, wherein the sides of the pouch are heat sealed at their edges.

4. The female panty condom of claim 1, wherein the front side of the pouch and the back side of the pouch are sewn together.

5. The female panty condom of claim 1, wherein a lip around the open end of the sheath is heat sealed to the front side of the pouch.

6. The female panty condom of claim 1, wherein a lubricant is included in the pouch.

7. The female panty condom of claim 1, wherein a cloth backing having an opening is affixed to the panty and over the back side of the pouch, such that the opening in the backing is aligned with the opening in the panty, and openings in the front and back side of the pouch.

8. The female panty condom of claim 1, wherein the pouch is affixed to the panty by clips.

9. The female panty condom of claim 1, wherein the pouch is sewn to the panty.

10. The female panty condom of claim 1, wherein a cloth backing having a slit is sewn to the pouch.

11. The female panty condom of claim 1, wherein a backing having a slit is affixed to the panty over the pouch such that the slit is aligned with the opening in the panty, the slit in the front side of the pouch and the slit in the back side of the pouch.

12. The female panty condom of claim 1, wherein the sheath is made from a polyolefinic material.

13. The female panty condom of claim 12, wherein the polyolefinic material is a low density polyethylene.

* * * * *